(12) United States Patent
Lee

(10) Patent No.: US 9,274,039 B2
(45) Date of Patent: Mar. 1, 2016

(54) PERMEAMETER FOR IN-SITU MEASUREMENT OF SATURATED HYDRAULIC CONDUCTIVITY

(71) Applicant: KOREA INSTITUTE OF GEOSCIENCE AND MINERAL RESOURCES, Daejeon (KR)

(72) Inventor: Bong Joo Lee, Daejon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 317 days.

(21) Appl. No.: 13/859,774

(22) Filed: Apr. 10, 2013

(65) Prior Publication Data
US 2014/0116114 A1    May 1, 2014

(30) Foreign Application Priority Data

Oct. 26, 2012    (KR) .................... 10-2012-0119620

(51) Int. Cl.
| | |
|---|---|
| *G01N 15/08* | (2006.01) |
| *G01N 33/24* | (2006.01) |
| *E21B 49/00* | (2006.01) |

(52) U.S. Cl.
CPC .............. *G01N 15/082* (2013.01); *E21B 49/00* (2013.01); *G01N 15/0806* (2013.01); *G01N 15/0826* (2013.01); *G01N 33/246* (2013.01)

(58) Field of Classification Search
CPC .............. G01N 33/246; G01N 15/082; G01N 15/0826; G01N 15/08; G01N 15/0806
USPC ............................................. 73/38
See application file for complete search history.

(56) References Cited

U.S. PATENT DOCUMENTS 6,412,528 B1 *    7/2002    Alex et al. .................... 141/323

OTHER PUBLICATIONS

Kelly et al., "Measuring the Hydraulic Conductivity of Shallow Submerged Sediments", Jul.-Aug. 2003, Ground Water, vol. 41.*
Landon et al., "Comparison of Instream Methods for Measuring Hydraulic Conductivity on Sandy Streambeds", Nov.-Dec. 2001, Ground Water, vol. 39.*
Landon, Rus, and Harvey, Comparison of Instream Methods for Measuring Hydraulic Conductivity in Sandy Streambeds, Natural Resources, School of, Papers in Natural Resources, University of Nebraska—Lincoln Year 2001.

* cited by examiner

*Primary Examiner* — Lisa Caputo
*Assistant Examiner* — Tran M Tran
(74) *Attorney, Agent, or Firm* — Justin H. Kim; Maxon Law Group

(57) ABSTRACT

A permeameter for in-situ measurement of saturated hydraulic conductivity is presented. The permeameter includes a chamber fixedly installed into streambed sediment such that the inside of the chamber is filled with a medium, sediment at water-sediment interface. First and second hydraulic head-measuring lines are respectively connected to upper and lower portions of an outer circumferential surface of the chamber, these are designed for measuring a hydraulic head difference of the inside of the chamber. A flexible tube is interconnected the chamber with the storage pipe. A storage pipe is designed to regulate a hydraulic head difference from the chamber and to measure a quantity and a flow rate of water introduced from the chamber under the streambed.

3 Claims, 7 Drawing Sheets

PERMEAMETER FOR IN-SITU MEASUREMENT OF SATURATED HYDRAULIC CONDUCTIVITY

CROSS-REFERENCE TO RELATED APPLICATIONS

This application claims priority to and the benefit of Korean Patent Application No. 10-2012-0119620 filed in the Korean Intellectual Property Office on Oct. 26, 2012, the entire contents of which are incorporated herein by reference.

BACKGROUND OF THE INVENTION

1. Field of the Invention

The present invention relates, in general, to a permeameter for in-situ measurement of saturated hydraulic conductivity of streambed sediments. The head difference between head within the chamber and head at the inlet of the pipe acts as the driving force to flow water from the chamber to the pipe. This head difference can be induced by adjusting the depth of the inlet in the pipe below stream stage. Water in a saturated zone around the chamber flows upwards through the sediments inside the chamber without electric power.

Upward flowing of water within the chamber causes a hydraulic head difference between the upper side and lower side of the chamber. In situ saturated hydraulic conductivity of the streambed sediment can be determined by measuring this hydraulic head difference in the chamber and an amount of water passing through the inside of the chamber.

2. Description of the Related Art

Generally, it is recognized that surface water and groundwater are resources that are interconnected and interact with each other so that physical and chemical changes in one affect physical and chemical composition/state of the other. Surface water-ground water interaction is an essential factor to be evaluated for purposes such as water budget analysis, understanding of passing routes of nutrients, contaminants, and investigation of groundwater flowing system, etc.

The interaction between the surface water and groundwater means discharge of groundwater from aquifer toward surface water, or recharge of the surface water into the aquifer. In order to evaluate the interaction between surface water and groundwater quantitatively, measurements for the hydraulic conductivity of streambed sediment, a hydraulic gradient between surface water and groundwater, and direct or indirect measurement of an amount of exchange between surface water and groundwater are needed. The hydraulic conductivity, i.e. a target object to be measured, is a value for a physical property that, like electric conductivity or thermal conductivity, is a measure of how well an aquifer substance allows water to pass therethrough. The hydraulic conductivity has a functional relationship with a porous medium and a fluid passing through the porous medium. The hydraulic conductivity of the porous medium is obtained using Darcy's law. Darcy's law is a constitutive equation that is formulated based on experimental researches on the flow of water through beds of sand, wherein groundwater flows from upper side toward lower side of a hydraulic head through the porous medium, and the flow rate of the groundwater is proportional to the hydraulic conductivity and hydraulic gradient. Hydraulic head is a specific measurement of liquid pressure above a geodetic datum. Hydraulic head of groundwater is expressed by the sum of an elevation head, a pressure head, and a velocity head. However, the velocity head may be ignored because generally the flow of groundwater is very slow. In an experimental apparatus (FIG. 1) for explaining Darcy's law, it can be seen that a flowing direction of groundwater is determined by a difference ($\Delta H$) in hydraulic heads of left and right water tanks, which are connected to a sand tank, irrespective of a position of the sand tank. In FIG. 1, when a datum level where z=0 is set, a hydraulic head $H_1$ of an A-sided water tank that amounts to the sum of an elevation head $Z_1$ and a pressure head $P_1$ is higher than a hydraulic head of a B-sided water tank ($H_2 = Z_2 + P_2$), so that it is shown that the flowing direction of groundwater is oriented from the A-sided tank of higher head toward the B-sided tank of lower head. Here, an amount Q of water passing through the sand tank is proportional to a difference in hydraulic heads ($\Delta H = H_2 - H_1$), a cross-section area A of the sand tank, and the time t elapsed, and is inversely proportional to a length L of the sand tank (Equation 1)

$$Q \approx -\frac{(H_2 - H_1)}{L} At \qquad \text{Equation 1}$$

If a proportional factor K is introduced, the Equation 1 can be expressed as following Equation 2.

$$Q = -K\frac{(H_2 - H_1)}{L} At \qquad \text{Equation 2}$$

The constant of proportionality K is called the hydraulic conductivity that depends both on characteristics of a fluid passing through a porous medium and porous medium itself. Here, $(H_2-H_1)/L$ is a hydraulic gradient.

The present invention relates to an apparatus for measuring hydraulic conductivity of sediment in a saturated zone of a water-sediment interface by measuring a quantity Q of groundwater passing through a chamber, which is inserted into sediment under a water-sediment interface, and a hydraulic gradient between two points within the chamber. Here, the saturated zone means a section where pores of porous medium are filled with groundwater, whereas the unsaturated zone means an air-permeable section that is ventilated above the surface of groundwater.

Generally, the saturated hydraulic conductivity of sediment under a water-sediment interface may be measured by a physical method and an estimating method using e.g. a tracer, modeling, or the like. The physical method is performed using a standpipe opening at both sides, which is inserted into sediment under the water-sediment interface, and includes a method using a constant head or falling head, a coupled method using a seepage flux and a hydraulic gradient between surface water and groundwater, a slug test, a grain size analysis and the like. It is evaluated that the physical method is a more economical than the estimating method like a tracer test or modeling. However, it has been reported that methods using the standpipe and seepage meter have problems of reduced reliability in terms of measuring results, the slug test has problems in that only horizontal hydraulic conductivity can be obtained, and the grain size analysis method has problems of using empirical formulae (Landon et al., 2001). Particularly, in the case of the standpipe method that directly measures the hydraulic conductivity of the streambed sediment in the field, water is introduced into the top of the standpipe, which is inserted into the streambed sediment that is a target object to be measured for hydraulic conductivity, so as to cause water to flow downwards through sediments within the pipe, thereby measuring the hydraulic conductivity in a manner of using a constant head or a falling head.

However, an apparatus and method of in-situ measuring of saturated hydraulic conductivity which causes water to flow upwards through sediment within chamber or pipe with or without power are not yet provided.

REFERENCE MATERIALS

Matthew K. Landon, David L. Rusy and F. Edwin Harveyz, 2001, Comparison of Instream Methods for Measuring Hydraulic Conductivity in Sandy Streambeds, Ground Water V. 39, No. 6, p. 870-885.

SUMMARY OF THE INVENTION

Accordingly, the present invention has been made keeping in mind the above problems occurring in the related art, and the present invention is intended to propose an apparatus for measuring hydraulic conductivity of sediment under a water-sediment interface with high reliability.

The above and other objects of the present invention will be described below, and will be understood with reference to embodiments of the invention. Further, the objects and advantages of the invention may be realized by means and combinations disclosed in claims.

In an aspect of the present invention, there is provided a permeameter for in-situ measurement of saturated hydraulic conductivity of streambed sediments. In the permeameter, a chamber and a storage pipe being interconnected via a flexible tube are vertically driven into a streambed while being spaced apart from each other. Here, in order to lower a hydraulic head of an inlet of the storage pipe relative to that of inside of the chamber, the storage pipe is fixedly inserted such that the depth of the inlet is lower than stage of surface water. A hydraulic head difference between the inlet of the storage pipe and the chamber causes water to flow from the chamber of higher hydraulic head towards the inlet of the storage pipe of lower hydraulic head. When the depth of the inlet of the storage pipe under the stage of surface water is fixed, a hydraulic head difference between upper and lower sides of the chamber and a flow rate per a unit area for a unit time (Darcy flux) become constant. The saturated hydraulic conductivity of streambed sediments may be calculated in the field by substituting the obtained hydraulic conductivity difference between the upper and lower sides of the chamber and Darcy flux to Equation 2.

As set forth in the foregoing, the present invention has the effect of directly measuring the hydraulic conductivity of sediment at water-sediment interface in the field.

Further, a chamber and a storage pipe are configured such that they are inserted into the sediment at water-sediment interface to provide a hydraulic head difference between the chamber and the storage pipe, thereby causing groundwater around the chamber to flow from the lower side towards the upper side within the chamber so that the hydraulic conductivity of the sediment in the chamber is effectively measured by measuring the amount of water flowing through the chamber and the hydraulic head difference between the upper and lower side of the chamber.

Further, during the flow rate of water passing through the chamber changes, phased hydraulic conductivity is measured by using phased hydraulic head difference between the upper and lower sides of the chamber, and the phased measuring results are compared with each other or functional relationship between phased Darcy fluxes and phased hydraulic gradients is checked, so that precision of the saturated hydraulic conductivity that was previously measured can be effectively verified in a overlapped manner.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE INVENTION

Figure 1:
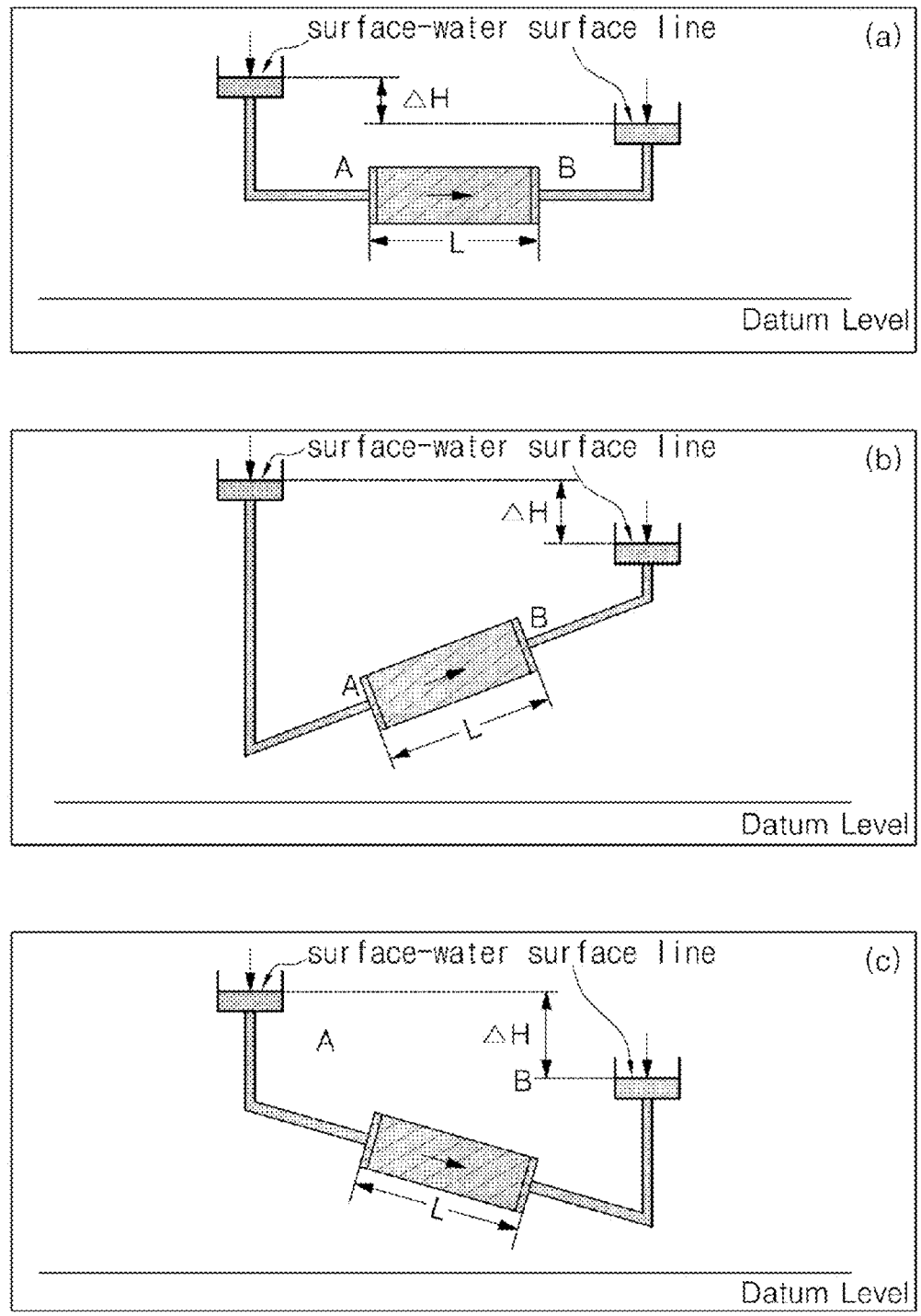
FIG. 1 is a view illustrative of a flowing direction of water in a tank, which depends on the difference in hydraulic head between the water tanks.
Figure 2:
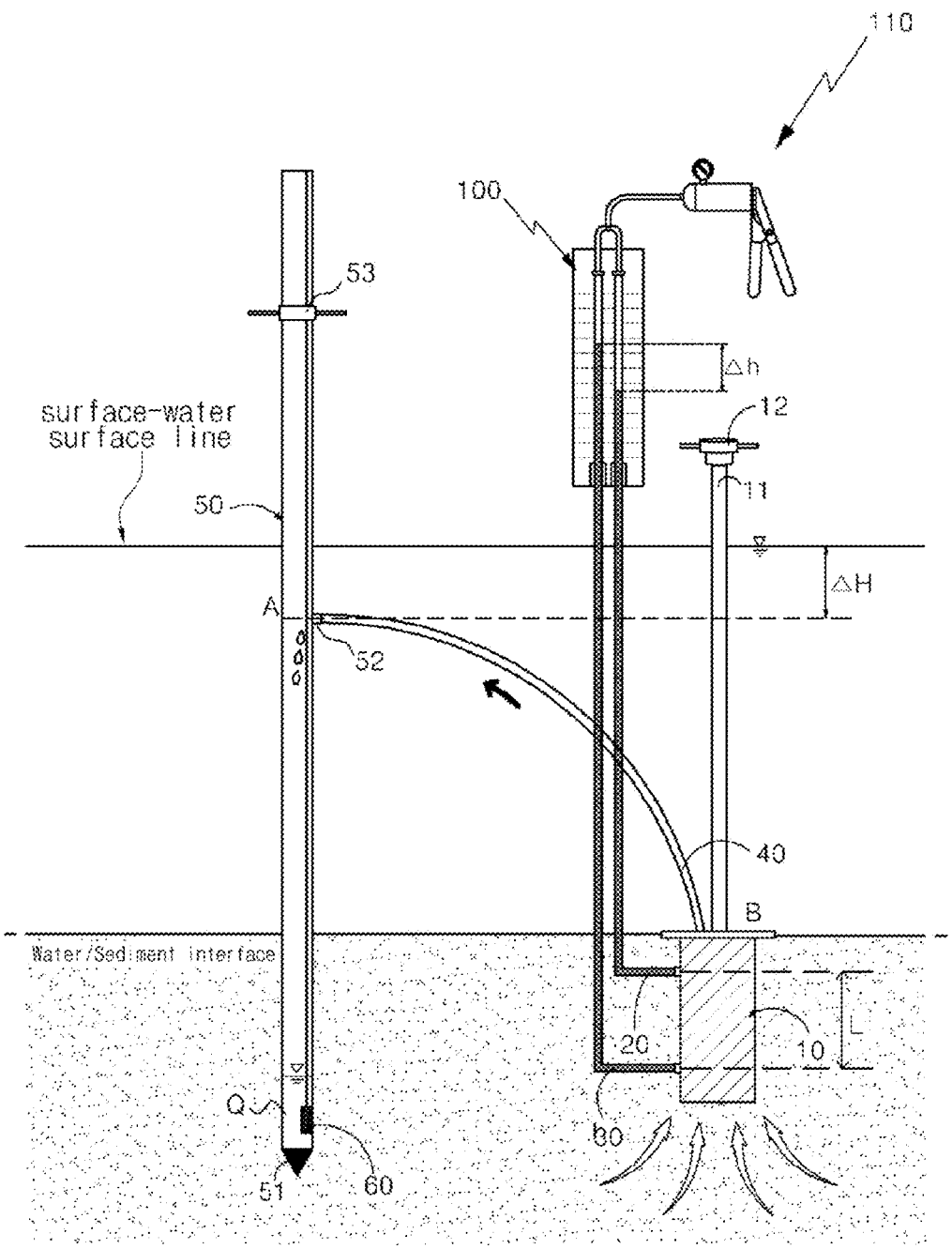
FIG. 2 is a schematic view showing a permeameter for in-situ measurement of saturated hydraulic conductivity according to the present invention.
Figure 3A:
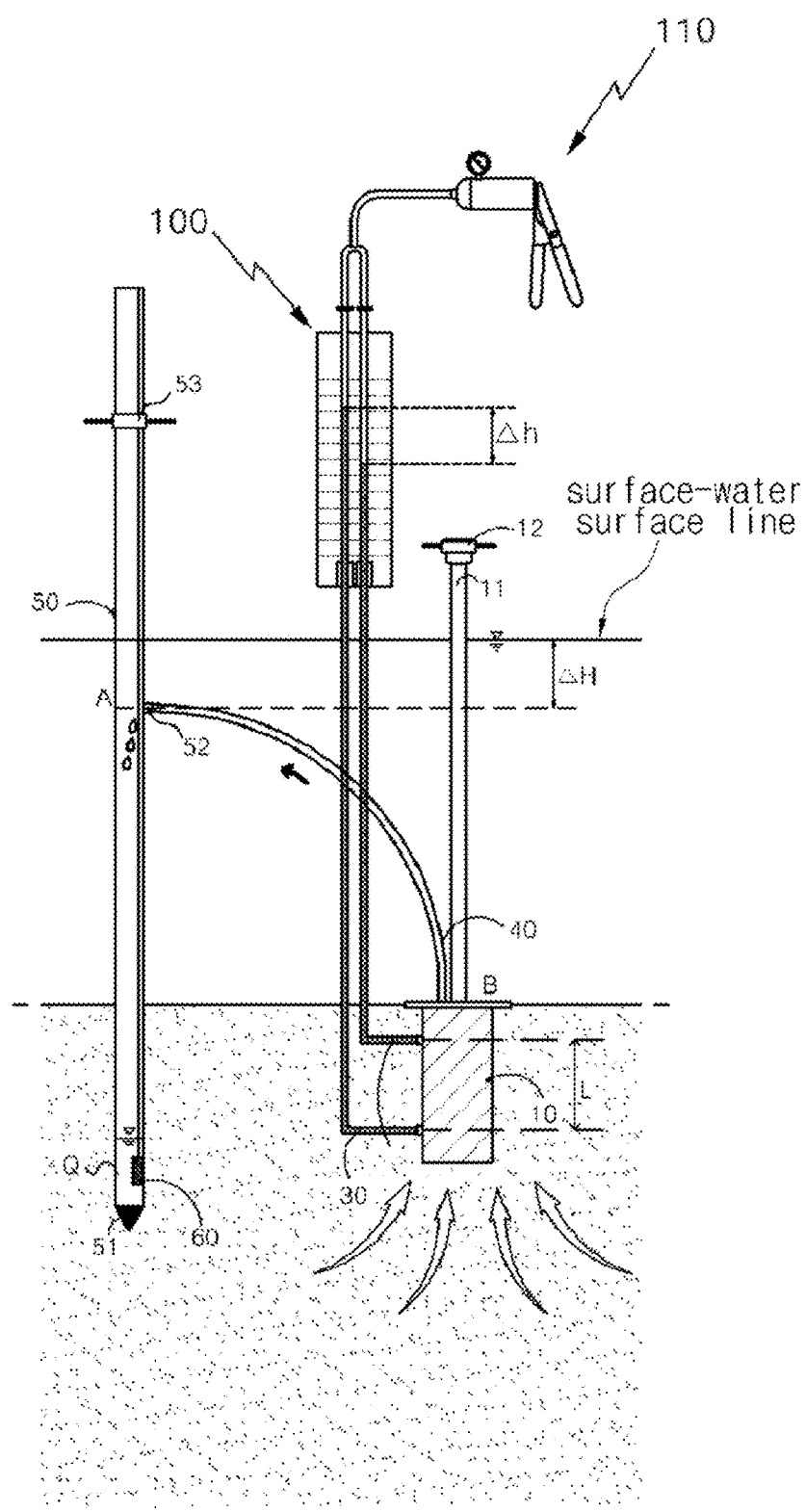
FIGS. 3(a), 3(b), and 3(c) show a front view showing variations in pressure head between an inlet of the storage pipe and the chamber, a hydraulic head difference between upper and lower sides of a 10 chamber, and Darcy flux in the permeameter according to an embodiment of the present invention.
Figure 3B:
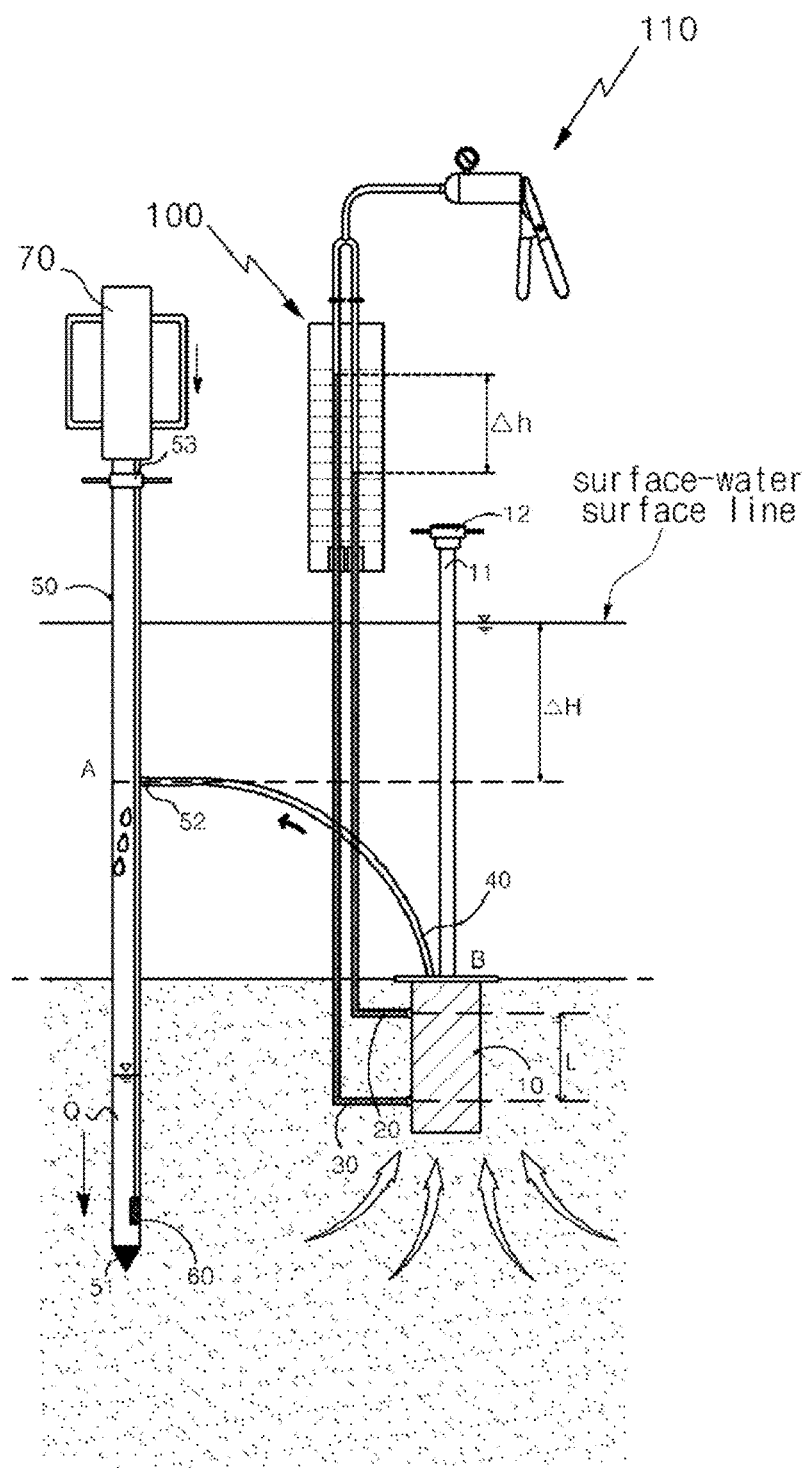
Figure 3C:
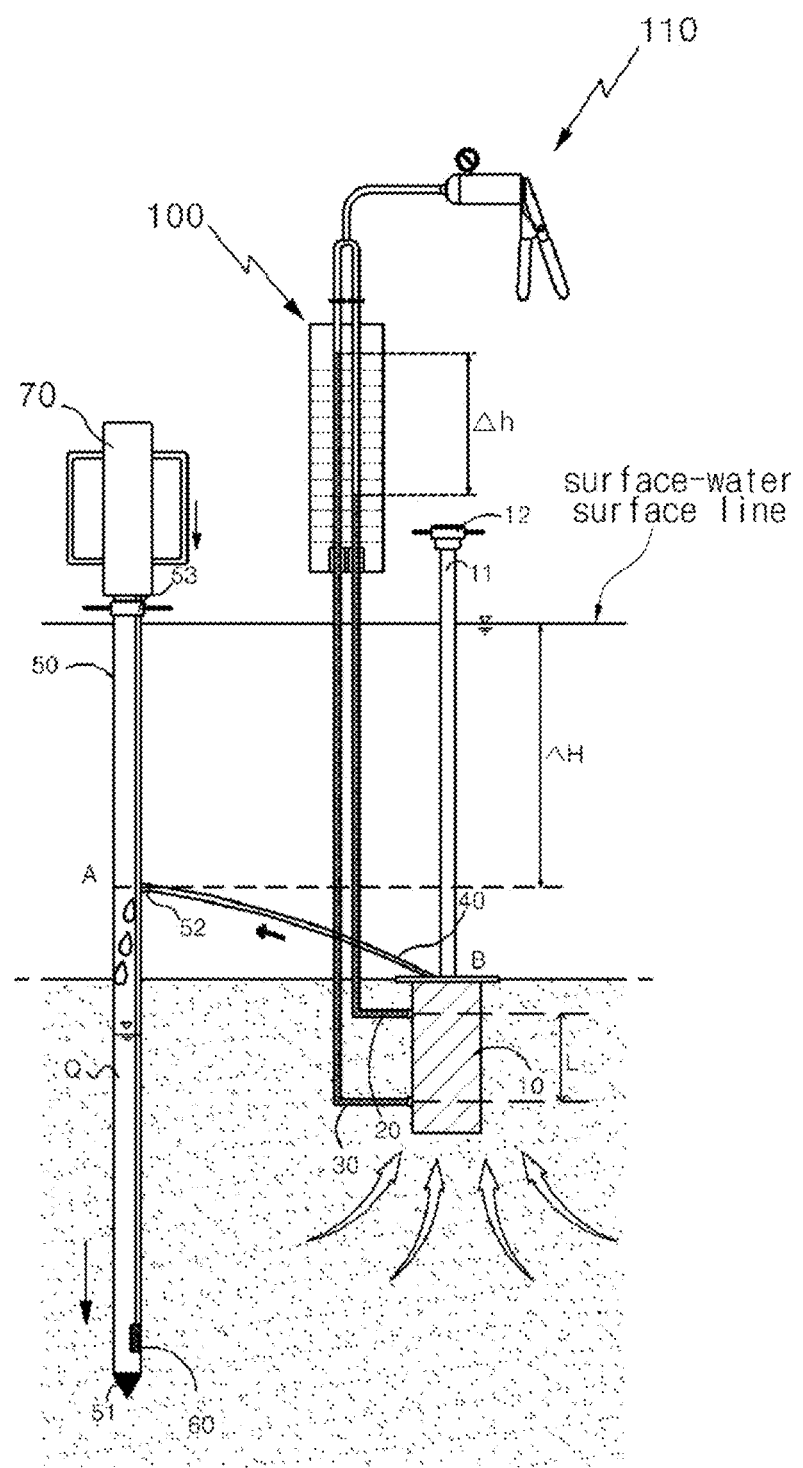

Prior to describing various embodiments in detail, it will be appreciated that the present invention is not limited to details on construction and arrangement of constitutional elements described in the description or illustrated in the drawings. The present invention may be realized and embodied into other embodiments and may be carried out in a variety of methods. Furthermore, it should be understood that directional terms about an apparatus or elements (such as "front", "back", "up", "down", "top", "bottom", "left", "right", "lateral", or the like) that are used herein are provided in order to merely simplify the description of the invention, and they do not mean that associated apparatus or elements should have such orientations.

The present invention has the following features for accomplishing the above objects of the invention.

Hereinbelow, preferred embodiments of the present invention will be described in detail with reference to the accompanying drawings. Prior to describing the embodiments, it will be further understood that terms or expressions used in the description and claims should not be construed as general or dictionary definitions, but should be construed as having meanings and concepts which are consistent with technical ideas of the invention based on principles that the inventors can properly define concepts of such terms for the best description of his/her invention.

Accordingly, embodiments and configurations described in this specification and drawings are merely most preferred embodiments of the invention and do not represent all the technical ideas of the invention, so that it should be understood that various equivalents and modifications able to substitute those technical ideas at the time when the present application was filed may be made.

Measurement of saturated hydraulic conductivity according to the present invention will now be described.

A chamber 10 and a storage pipe 50 which are interconnected via a connection line 40 are vertically installed into a streambed such that they are spaced apart from each other. When mounting the chamber 10, the chamber 10 should be inserted into the streambed slowly in order to prevent sediment from being disturbed, and the depth of the storage pipe 50 being inserted should be determined such that the depth of an inlet 52 of the pipe is a fixed depth that is lower than the surface-water surface.

When the storage pipe 50 is vertically inserted into the streambed such that the depth of the inlet 52 thereof is lower than the surface-water surface, a hydraulic head difference ($\Delta H$) is generated between the inlet 52 and the chamber 10, which causes a water flow from the chamber 10 inserted into the streambed towards the inlet 52 of the storage pipe 50. This means that groundwater around the chamber 10 flows into the chamber 10, resulting in water flowing from the lower side toward the upper side of the chamber 10 and causing a hydraulic head difference ($\Delta h$) between the lower and upper sides of the chamber. If the depth of the inlet 52 of the storage pipe 50 under the groundwater surface is fixed, a flow rate of water flowing through the chamber and the hydraulic head difference ($\Delta h$) between the upper and lower sides of the chamber are maintained constant, so that hydraulic conductivity can be obtained by measuring the flow rate and the hydraulic head difference and calculating a ratio thereof (according to Darcy's law, the hydraulic conductivity is a ratio of Darcy flux to a hydraulic gradient).

Further, if the depth of the inlet 52 of the storage pipe 50 under the surface water surface is made deeper stepwise, a hydraulic head difference ($\Delta H$) between the chamber 10 and the inlet 52 also increases stepwise, so that a flow rate Q of water flowing from the lower side toward the upper side of the chamber 10, and the hydraulic head difference ($\Delta h$) between the lower and upper sides of the chamber also increase proportionally. Phased hydraulic conductivities each mean a ratio of Darcy fluxes to phased hydraulic head differences ($\Delta h$) of the upper and lower sides of the chamber 10. Since hydraulic conductivity of a porous medium in the chamber that is a target medium to be measured is a characteristic value, phased hydraulic conductivities obtained stepwise should also be identical. This means that a comparison between phased hydraulic conductivities obtained stepwise becomes a means for verifying precision of in-situ measurement of saturated hydraulic conductivity according to the invention in an overlapped manner.

An exemplary embodiment of in-situ measurement of saturated hydraulic conductivity will be described with reference to FIGS. 1 to 5.

As shown in the drawings, a permeameter for in-situ measurement of saturated hydraulic conductivity according to the present invention measures Darcy flux which flows depending on a degree of hydraulic gradient that is artificially induced, and analyzes a relationship between the hydraulic gradient and the Darcy flux, thereby calculating saturated hydraulic conductivity of a streambed. The permeameter includes a chamber 10, first, second hydraulic head-measuring lines 20 and 30, a connection line 40, and a storage pipe 50.

The chamber 10 is a hollow cylindrical drum, a lower end of which is open. The chamber 10 is vertically installed into the sediment under a water-sediment interface by slowly pressing an upper portion of the chamber downwards. Thereby, a medium such as sand and clay in the saturated zone fills the chamber through the open lower end. An extension pipe 11 extending out of the water surface is vertically mounted to the upper portion of the chamber 10, and a horizontal bar 12 perpendicular to the extension pipe 11 is further mounted to the uppermost end of the extension pipe 11 in order to identify whether or not the chamber 10 has been mounted in a vertical position relative to a surface water-sediment interface by checking the horizontal position of the horizontal bar 12. The horizontal bar 12 can also serve as a grip which is used when the chamber 10 is mounted or removed.

The lower ends of the first and second hydraulic head-measuring lines 20 and 30 are connected to upper and lower portions of an outer circumferential surface of the chamber, and the other ends extend out of the water surface and are connected to the manometer 100. Here, the first hydraulic head-measuring line 20 is the line that is connected to the upper portion of the outer circumferential surface of the chamber 10, and the second hydraulic head-measuring line 30 is the line that is connected to the lower portion of the outer circumferential surface of the chamber 10 (i.e. the position of the second line is lower than that of the first line 20 on the outer circumferential surface of the chamber 10). The first and second hydraulic head-measuring lines 20 and 30 are provided for measuring a hydraulic head difference ($\Delta h$) between two points in the chamber, which occurs due to head loss when water flows from the lower side toward the upper side of the chamber 10 (e.g. using a manometer 100, a hand vacuum pump 110, and the like). The lower ends of the first and second hydraulic head-measuring lines 20 connected to the chamber 10 are covered with mesh filters in order to prevent an inflow of sediment contained in the chamber 10.

The connection line 40 is a flexible tube, one end of which is communicatingly connected to the upper end of the chamber and the other end of which is communicatingly connected to an inlet 52 provided to an outer circumference of the storage pipe 50 which will be described later. Thereby, water flowing through the chamber 10 is introduced into the inlet 52 (where a nozzle is mounted to communicate with the connection line 40) via the connection line 40, filling the storage pipe 50.

The storage pipe 50 is an upper-open ended hollow cylindrical pipe with a circular section, which is provided at a lower end with an inversely conical inserting section 51 that is gradually pointed at the other end for easy mounting as it goes downwards. The storage pipe 50 is directly fixedly inserted into the streambed vertically while being spaced apart from the chamber 10. The pointed inserting section 51 of the storage pipe 50 is fixedly inserted into the streambed such that an open upper portion of the storage pipe extends out of the water surface so that the surface water cannot be introduced into the storage pipe via the open upper end. The depth of the storage pipe 50 under the surface water surface is regulated by striking a pressing piece 53, which extends out of the outer circumferential surface of the storage pipe, with a slide hammer, a means for pressing the pressing piece.

Since the storage pipe 50 has a constant cross-section area, if a change in the level of water introduced into the storage pipe 50 is measured, it can be checked whether an amount and an inflow rate of water are constant or not. Since if the inflow rate of water introduced into the storage pipe 50 is constant, the change in the water level in the storage pipe 50 linearly increases, Darcy flux can be measured by selecting a water level-change section that linearly increases, and obtaining elapsed time and a total amount of inflow water within the selected section. The water level-change in the storage pipe is obtained using an automatic water gauge 60 which is installed on the bottom of the storage pipe 50. Darcy flux and the hydraulic head difference ($\Delta h$) between the upper and lower sides of the chamber 10 are essential elements for calculating saturated hydraulic conductivity of the sediment using equation 2.

As previously mentioned, the storage pipe 50 is provided on its outer circumferential surface with the inlet 52, to which one end of the connection line 40 is connected to the chamber. Here, a hydraulic head difference (ΔH) between the inlet 52 of the storage pipe 50 and the chamber 10 is regulated by adjusting the position of the inlet 52 of the storage pipe 50, i.e. the position to which one end of the connection line 40 is connected. As the position of the inlet to which the connection line 40 is connected is increasingly lowered, the hydraulic head difference (ΔH) between the inlet 52 of the chamber 10 increases. Thereby, the quantity Q of water introduced into the storage pipe 50 is also increased. Further, the permeameter of the invention is also configured such that after the depth of the inlet 52 of the storage pipe 50 is made deeper stepwise, Darcy fluxes discharged from the chamber 10 and the hydraulic head differences (Δh) between the upper and lower sides of the chamber 10 are measured so as to calculate saturated hydraulic conductivity of sediment for each phase. Since hydraulic conductivity of a porous medium in the chamber 10 that is a target medium to be measured is an intrinsic value, hydraulic conductivities obtained stepwise should also be identical if measured precisely. And hydraulic gradients and Darcy fluxes measured stepwise should have a linear functional relationship therebetween. Thereby, the precision of the hydraulic conductivities obtained by the permeameter of the invention can be verified in an overlapped manner by simply comparing hydraulic conductivities obtained stepwise each other, and checking whether hydraulic gradients and Darcy fluxes measured stepwise have a linear functional relationship, and whether a linear gradient of such a linear function coincides with hydraulic conductivity that was already checked.

Figure 4:
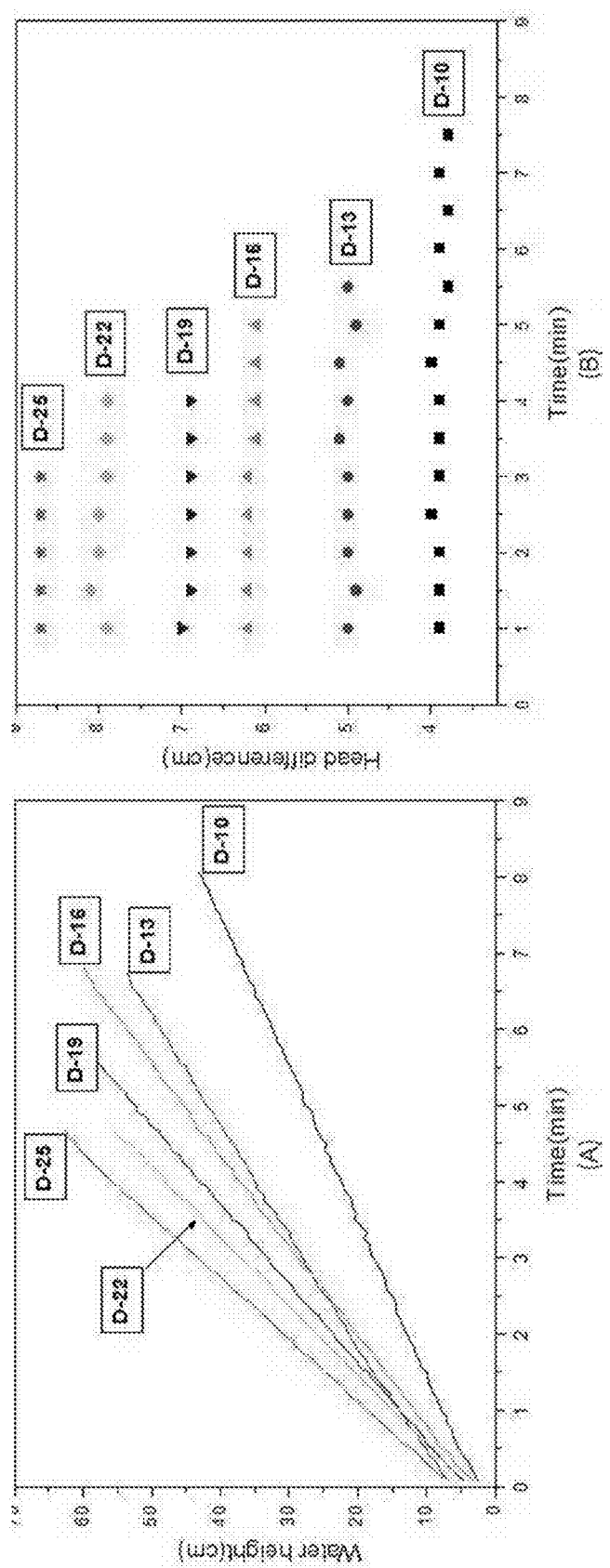
FIG. 4 is a graphical diagram showing phased flow rates and phased hydraulic conductivities between the upper and lower sides of the chamber, which are measured using the permeameter according to the present invention.
Figure 5:
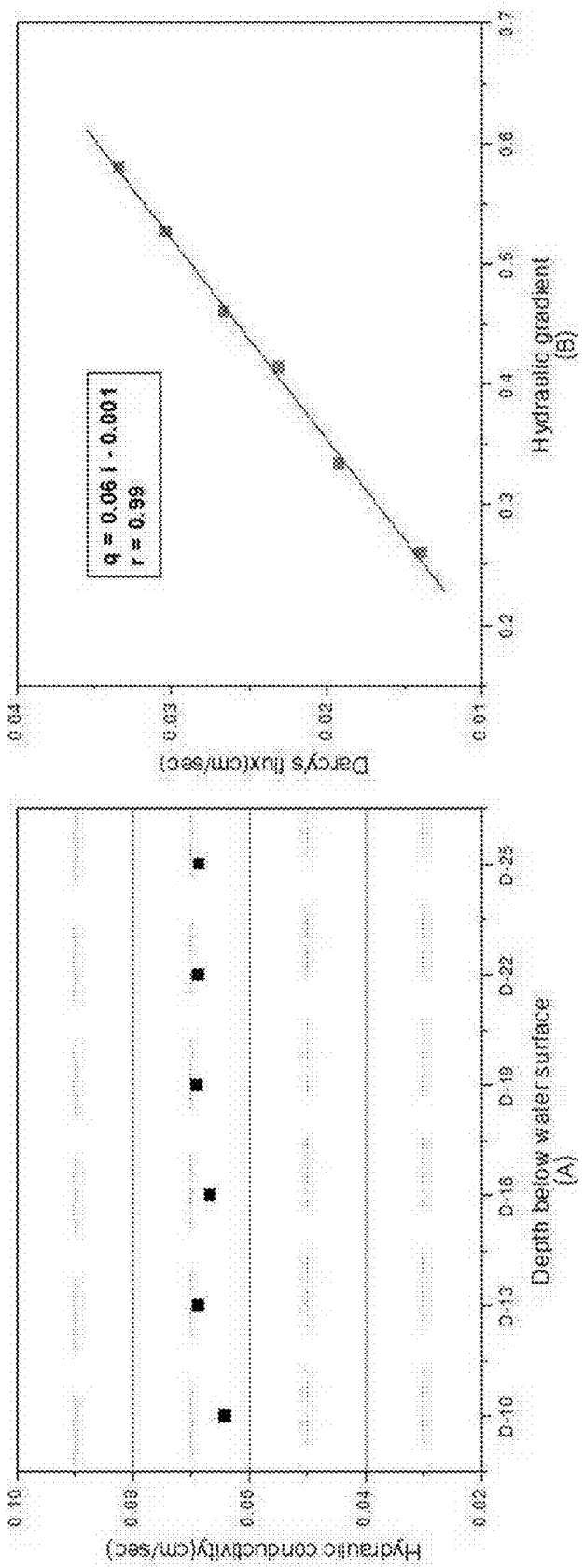
FIG. 5 is a graphical diagram showing phased hydraulic conductivities measured by the permeameter according to the present invention, and a functional relationship between phased hydraulic gradients and Darcy flux.

FIGS. 4 and 5 show results of in-situ measurements of the hydraulic conductivity streambed sediment at water-sediment interface with the permeameter of the invention in field. The chamber 10 vertically inserted into the streambed sediment has an inner diameter of 10.8 cm and a length of 25.0 cm, and a spaced distance between the lower ends of the first and second hydraulic head-measuring lines connected to the chamber 10 is 15.0 cm. The hydraulic conductivity was first measured in the state that the storage pipe 50 (inner diameter of 4.8 cm) was inserted into the streambed such that the depth of the inlet 52 under the surface water surface is fixed to 10 cm. Then, hydraulic conductivities were measured stepwise while increasing the depth of the inlet 52 of the storage pipe 50 by 3 cm at a time for 6 times such that a final depth reaches 25 cm under the surface water surface.

FIG. 4A shows changes in the level of water introduced into the storage pipe 50. Here, it could be seen that the stepwise change in water level was substantially linear. And as the depth under the surface water surface increases, a rising rate of water level was increasingly high. The linear change in the water level means that an inflow of water per unit time is constant. An increase of rising rate of water level according to an increase of the depth is caused by the increase in the inflow of water introduced into the storage pipe 50 due to the increase in the hydraulic head difference (ΔH) between the chamber 10 and the storage pipe 50. FIG. 4B shows measured results of stepwise hydraulic head differences (Δh) between the upper and lower sides of the chamber 10 relative to time elapsed when measuring stepwise hydraulic conductivities. Here, it could be seen that the phased hydraulic head differences (Δh) between the upper and lower sides of the chamber 10 were maintained substantially constant as the time elapsed, and as the depth of the inlet 52 of the storage pipe under the groundwater increases, phased hydraulic head differences (Δh) between the upper and lower sides of the chamber 10 were increased. These results mean that stepwise water flow flowing through the chamber 10 is stable.

FIG. 5A shows measured results of hydraulic conductivities which were obtained using Darcy fluxes and phased hydraulic head differences (Δh) between the upper and lower sides of the chamber 10 measured at each step. Here, it could be seen that the hydraulic conductivities have substantially the same values (0.06 cm/sec) irrespective of phases. FIG. 5B shows that phased Darcy fluxes and hydraulic gradients have a linear functional relationship. From the Darcy's law, a gradient of this linear function means the hydraulic conductivity of the streambed sediment. It was checked that the value of 0.06 cm/sec was the same as the value which was obtained by comparing phased hydraulic conductivities. Such results means that measured results of saturated hydraulic conductivity measured according to the present invention is precise, and the precision can be verified autonomously.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A permeameter for in-situ measurement of saturated hydraulic conductivity, comprising: a chamber fixedly installed into a streambed such that the inside of the chamber is filled with sediment, wherein a lower end of the chamber is open; first and second hydraulic head-measuring lines respectively communicatingly connected to upper and lower portions of an outer circumferential surface of the chamber for measuring a hydraulic head difference within the chamber; a storage pipe designed to regulate a hydraulic head difference from the chamber and to measure a quantity and a flow rate of water introduced from the chamber under the streambed; and a connection line which is a flexible tube and whose one end is communicatingly connected to an upper end of the chamber and the other end is communicatingly connected to an outer circumference of the storage pipe such that water flowing through the chamber is introduced into the connection line so that the water finally fills the storage pipe, wherein the storage pipe being installed at a distance from the chamber such that one end of the storage pipe is fixed into the streambed.

2. The permeameter according to claim 1, wherein the hydraulic head difference between the chamber and the storage pipe is regulated by adjusting the depth of the storage pipe under surface-water surface in the field of a target streambed, such that water flows from the chamber from the lower side toward the upper side and then to the storage pipe, without power.

3. The permeameter according to claim 1, wherein the precision of measured results on the hydraulic conductivity is verified by selecting one of the three means as follows: (1) a comparison of phased hydraulic conductivities obtained when the depth of the inlet of the storage pipe under the surface water is changed stepwise; (2) checking whether phased hydraulic gradients and Darcy fluxes have a linear functional relationship or not; and (3) checking whether or not a linear gradient of the linear function formed between the phased hydraulic gradients and Darcy fluxes coincides with the hydraulic conductivities checked in the above items (1) and (2).

* * * * *